US005792793A

United States Patent [19]
Oda et al.

[11] Patent Number: 5,792,793
[45] Date of Patent: Aug. 11, 1998

[54] ANTIBACTERIAL, ANTIFUNGAL AND ANTIVIRAL AGENT

[75] Inventors: Munehiro Oda; Hiroyuki Itoh; Tetsushi Sudo; Sadatoshi Sakuma, all of Odawara; Kenji Nomiya, Hadano; Yasunori Suzuki, Odawara; Yukiyoshi Jonoshita, Tokyo; Akira Kikuchi, Tokyo; Yoshiko Takabatake, Tokyo, all of Japan

[73] Assignees: Meiji Milk Products Co., Ltd.; Toyo Ink Mfg. Co., Ltd., both of Tokyo, Japan

[21] Appl. No.: 635,958

[22] PCT Filed: Oct. 7, 1994

[86] PCT No.: PCT/JP94/01684

§ 371 Date: May 6, 1996

§ 102(e) Date: May 6, 1996

[87] PCT Pub. No.: WO95/12602

PCT Pub. Date: May 11, 1995

[30] Foreign Application Priority Data

Nov. 5, 1993 [JP] Japan ................ 5-276471
May 30, 1994 [JP] Japan ................ 6-116909
Jun. 17, 1994 [JP] Japan ................ 6-135523

[51] Int. Cl.$^6$ ................ A61K 31/28; C07F 1/08
[52] U.S. Cl. ................ 514/495; 106/1.05; 556/113; 556/117; 548/101
[58] Field of Search ................ 556/113, 117; 514/495; 106/1.05; 548/101

[56] References Cited

FOREIGN PATENT DOCUMENTS 156103   3/1922   United Kingdom .
465291   5/1937   United Kingdom .

OTHER PUBLICATIONS

Chemical Abstracts, vol. 76, Abstract No. 7287, 1971.
Chemical Abstracts, vol. 112, Abstract No. 213767, 1989.
Chemical Abstracts, vol. 78, Abstract No. 78098, 1972.
Chemical Abstracts, vol. 116, Abstract No. 74848, 1991.
Chemical Abstracts, vol. 108, Abstract No. 171272, 1988.
Chemical Abstracts, vol. 107, Abstract No. 224060, 1987.
Chemical Abstracts, vol. 83, Abstract No. 143892, 1975.
Chemical Abstracts, vol. 92, Abstract No. 223338, 1980.
Chemical Abstracts, vol. 117, Abstract No. 261736, 1992.

*Primary Examiner*—Porfirio Nazario-Gonzalez
*Attorney, Agent, or Firm*—Oblon, Spivak, McClelland, Maier & Neustadt, P.C.

[57] ABSTRACT

The present invention relates to a complex formed by the coordination between a thiol group-containing compound and a silver ion; an antibacterial, antifungal, and antiviral agent containing the same as the active agent; and an antibacterial, antifungal, and antiviral composition containing the above agent and a vehicle or a carrier.

The agent has a wide antibacterial and antifungal spectrum and an antiviral activity, is well compatible with various vehicles and carriers, sustains its activity for long, and has reduced peroral toxicity, skin irritation and mucosa irritation.

27 Claims, No Drawings

ANTIBACTERIAL, ANTIFUNGAL AND ANTIVIRAL AGENT

TECHNICAL FIELD

The present invention relates to antibacterial, antifungal, and antiviral agents as well as to compositions containing the agents. More particularly, the present invention relates to antibacterial, antifungal, and antiviral agents having wide antibacterial spectra, resisting against decomposition, exhibiting sustained activities, and being very safe providing reduced skin irritation and mucosa irritation. The invention also relates to compositions which contain the agents and which can be used in a wide variety of industrial fields.

BACKGROUND ART

In recent years, many attempts have been made to exploit compositions exhibiting antibacterial and antifungal activities in the fields of textiles, sanitary goods, tableware, packaging materials, paints, sprays, etc. These compositions acquire a function of providing antibacterial and antifungal activities when chemicals exhibiting antibacterial and antifungal activities are added to, or kneaded together with, a variety of vehicles or carriers.

In order for chemicals exhibiting antibacterial and antifungal activities to be exploited in a wide range of industrial fields, they must be safe and have wide antibacterial and antifungal spectra. Moreover, they must satisfy requirements with respect to compatibility with vehicles and carriers, durability, sustained activities, and economy.

Examples of chemicals used as antibacterial and antifungal agents include benzimidazoles, nitriles, isothiazolines, haloallylsulfones, iodopropargyls, benzthiazoles, phenols, and organic tins, pyridines, diphenylethers, and chlorhexidines.

However, many of these antibacterial and antifungal agents do not provide sufficient antibacterial and antifungal effects. Moreover, even though certain chemicals exhibit exellent antibacterial and antifungal activities, they may not always possess excellent compatibility with vehicles or carriers, and in such cases, they may eventually exhibit only poor antibacterial and antifungal activities when they are actually used in various industrial fields. On the other hand, regarding the safety of these antibacterial and antifungal agents, it is noted that many of them induce peroral toxicity, skin irritation, and mucosa irritation. In general, the stronger the antibacterial and antifungal activity, the more significant these actions. Therefore, in order to exploit compositions containing antibacterial and antifungal agents in everyday life environments, the above problems must be solved.

Accordingly, an object of the present invention is to provide antibacterial, antifungal, and antiviral agents which have wide antibacterial and antifungal spectra, are well compatible with vehicles and carriers, exhibit resistance against decomposition; sustain their activities, and have reduced peroral toxicity, skin irritation, and mucosa irritation effects.

DISCLOSURE OF THE INVENTION

The present inventors conducted extensive studies, and found that a complex formed by the coordination of a thiol-group containing compound with a silver ion exhibits a wide antibacterial and antifungal spectrum and also exhibits antiviral activity, that the complex is well compatible with various vehicles and carriers, and that the complex has significantly reduced toxicity, skin irritation, and mucosa irritation effects, leading to completion of the invention.

Accordingly, the present invention provides a complex formed by the coordination between a thiol-group containing compound and a silver ion.

The present invention also provides an antibacterial, antifungal, and antiviral agent comprising, as an active component, a complex formed by the coordination between a thiol-group containing compound and a silver ion.

The present invention also provides an antibacterial, antifungal, and antiviral composition comprising a complex formed by the coordination between a thiol-group containing compound and a silver ion, as well as a vehicle or a carrier for the complex.

BEST MODE FOR CARRYING OUT THE INVENTION

In the complex of the present invention, the thiol-group containing compound to be coordinated with a silver ion is not particularly limited; any thiol group-containing compounds may be used in this invention, so far as they are organic compounds such as saturated or unsaturated hydrocarbons or heterocyclic compounds. The organic compounds may contain, in addition to thiol groups, functional groups such as carboxyl groups, hydroxyl groups, amino groups, or halogens. Examples of saturated hydrocarbons include C1–C30 linear, branched, or cyclic alkyl groups. Examples of unsaturated hydrocarbons include C2–C30 linear, branched, or cyclic alkenyl groups and aromatic hydrocarbon groups. Examples of heterocyclic compounds include C5–C30 monocyclic or condensed ring-type compounds having oxygen, nitrogen, or sulfur atoms as the heterologous atoms.

Specific examples of the thiol group-containing compounds include thiosalicylic acid and its salts, p-toluene thiol, 2-naphthalene thiol, thiomalic acid, thioglycollic acid, α-thiolactic acid, β-thiolactic acid, cysteine, thioglycerol, sodium 5-mercapto-(1H)-tetrazolyl acetate, 2-mercaptoethanol, 2,3-dimercaptosuccinic acid, thiophenol, 2-mercaptobenzimidazole, 2-mercaptobenzothiazole, thiourea, mercaptonicotinic acid, 2-thiouracil, and 2-mercaptohypoxanthine. Of these, thiosalicylic acid and its salts are particularly preferred.

The complex of the present invention is preferably formed by the coordination between 0.1–4 mol, particularly 0.5–2 mol, of a thiol group-containing compound, and 1 mol of silver. Also, it is preferred that a counter cation to be added to the complex take the form of an alkali metal cation or an alkaline earth metal cation. $K^+$, $Na^+$, $Ca^{++}$, and $Ba^{++}$ are particularly preferred.

The complex of the present invention may be prepared by, for example, reacting a thiol group-containing compound with a silver ion in an aqueous solution, and then by adding alcohol or other materials to the resultant solution so as to cause precipitation of a complex.

Preferred silver compounds to be used in the present invention are water-soluble silver salts.

It is preferred that 0.1–4 mol, particularly 0.5–2 mol, of a ligand be reacted with 1 mol of silver and that the pH during reaction be between 0.5 and 13.5.

The thus-obtained complex of the present invention (hereinafter referred to as the thiol-silver complex or more simply the complex), which exhibits excellent antibacterial, antifungal, and antiviral activities, may be directly used as an antibacterial agent, antifungal agent, or an antiviral agent.

However, if the thiol-silver complex is blended with a variety of vehicles or carriers so as to formulate antibacterial, antifungal, and antiviral compositions, such compositions can be used in a wide variety of industrial fields.

The vehicles and carriers may be solids, liquids, or mixtures of solids and liquids.

Solid vehicles and solid carriers may be either inorganic or organic. Examples of inorganic solid carriers include metal, glass, ceramics, silica, hydroxyapatite, zeolite, and titanium dioxide. In compositions comprising any of these inorganic solid carriers and a thiol-silver complex, it is preferred that the thiol-silver complex be anchored onto the solid carrier. In order to anchor a thiol-silver complex to a carrier, thermal processing and chemical bonding are preferably employed.

A composition of the present invention comprising an inorganic solid carrier as described above and a thiol-silver complex is free from drawbacks inherent to conventional silver-containing antibacterial agents led by zeolite-silver agents, without inviting discoloration of silver ion due to exposure to light and without diminishing antibacterial activities due to a substitution reaction in the presence of a salt. Examples of organic solid vehicles and carriers include waxes and resins. Useful waxes are those which are capable of being dispersed in water, and they may be animal, vegetable, mineral, or synthetic waxes.

Examples of animal waxes include beeswax; vegetable waxes include carnauba wax, candelilla wax, wood wax, ouricury wax, wax from the bark of Douglas fir, rice bran wax, jojoba wax, and bebeeru wax; and mineral waxes include montan wax, peat wax, ozokerite-ceresine wax, and petroleum waxes (for example, paraffin wax, and paraffin-microcrystalline-semicrystalline wax). Examples of synthetic waxes include polyethylene waxes, polyethylene chloride waxes, Fischer-Tropsch wax, chemically modified hydrocarbon waxes, and substituted amide waxes. Of the listed waxes, synthetic waxes are preferably used in view of their excellent gloss-imparting ability and ease in coating operation. In the production of compositions for floor polishing, use of vegetable waxes is preferred in view of their good compatibility with emulsions.

Resins may be natural, semisynthetic, or synthetic ones. They may be thermoplastic or setting.

Examples of thermoplastic resins include polyethylenes, polypropylenes, vinyl chlorides, acrylonitrile-butadiene-styrene copolymer resins, ethylene-vinyl acetate copolymer resins, nylons, polyesters, polyvinylidene chlorides, polyamides, polystyrenes, polyacetals, polyvinyl alcohols, polycarbonates, acrylic resins, fluorine resins, polyurethane resins, rayon, and cupra.

Examples of setting resins include phenol resins, urea resins, melamine resins, unsaturated polyester resins, epoxy resins, polyvinyl alcohols, acrylic polyols, polyisocyanates, and functional group-containing polyesters. The setting mechanism of the setting resins may utilize heat or energy beams.

Compositions of the present invention comprising the above-described waxes or resins and thiol-silver complexes may be prepared by simply mixing them, or alternatively, by dispersing thiol-silver complexes in waxes or resins.

Although compositions in a dispersed state may be prepared by directly dispersing a predetermined amount of thiol-silver complex in a resin or wax, it is preferred that a master batch be used for enhancing dispersibility. Briefly, a complex, solely or in combination with a common dispersant if needed, is predispersed in a resin (or wax) at a high concentration (master batch), and the resultant master batch is diluted using either the same resin (or wax) or a resin (or wax) highly compatible with the resin (or wax) to adjust the concentration of the thiol-silver complexes. The amount of a complex in the master batch is preferably not less than 5% by weight, and more preferably 10–80% by weight.

In more detail, compositions in a dispersed state can be obtained by dispersing at least one species of thiol-silver complex throughout a resin (or wax) using any or several of mechanisms capable of providing shear forces such as dual rollers, triple rollers, kneaders, extruders, colloidal mills, homomixers, or ball mills. When thermoplastic resins are used, heat is suitably applied in consideration of the melting point or the softening point of the resin. Alternatively, when thermosetting or energy beam-setting resins are used, they are dispersed without applying heat; solely in the presence of shear forces, thereby obtaining compositions in a dispersed state.

Examples of liquid vehicles and carriers include various organic solvents and aqueous solvents, with aqueous solvents being particularly preferred. Preferred aqueous solvents are water and solutions or dispersions in which resins (aqueous binders) are dissolved or dispersed in water. Aqueous binders may be water-dispersible resins or water-soluble resins. Specific examples of aqueous binders include polyvinyl alcohols, acrylic resins, urethane resins, polyester resins, amino resins, and vinyl resins. Of these, polyvinyl alcohols and acrylic resins are particularly preferred.

The above-described compositions prepared through incorporating a thiol-silver complex in liquid vehicles or carriers are suitable as antibacterial, antifungal, and antiviral liquids or as antibacterial, antifungal, and antiviral sprays.

Sprays may be prepared by charging, together with a propellant, a neat liquid obtained by dissolving or dispersing a thiol-silver complex (0.5–30% by weight) in an aqueous medium in aerosol containers. The neat liquid may further contain, if necessary, other antibacterial substances, surfactants, and perfumes. Under normal circumstances, it is preferred that the amount of a thiol-silver complex serving as an active component of an antibacterial, antifungal, and antiviral spray composition be approximately 0.5% by weight or more.

When spray compositions are prepared, water may generally be used as the liquid vehicle or carrier. However, depending on end uses, other substances may be used, including ethanol, propanol, isopropanol, kerosene, acetone, and their mixtures. Examples of propellants include liquified $CO_2$ gas, freon gas, and nitrogen gas. Propellants are usually used in amounts such that the achieved pressure at 20° C. is 1.0–7.4 kg/cm$^2$, preferably 2.0–6.0 kg/cm$^2$. Aerosol containers may be known ones, containers for compressed gases, or plastic containers equipped with a manual pump for jetting discharge.

The antibacterial, antifungal, and antiviral compositions of the present invention may be used in combination with other antibacterial substances. Other antibacterial substances which may be co-used include alcohols such as ethyl alcohol and antibacterial substances of animal and vegetable origin. Amounts of such substances are suitably determined depending on purposes of use. For example, if ethyl alcohol is co-used, its amount is preferably not more than approximately 10% by weight.

Examples of surfactants include various soaps, higher alcohol sulfates, fatty acid glycerides, and sorbitan fatty acid esters.

Antibacterial, antifungal, and antiviral spray compositions of the present invention are very safe, and therefore, they can be used in a wide variety of applications including foods, bathrooms which are frequently used by people in a contacting manner, inside walls of refrigerators and rooms, carpets, and tatami mats to prevent damage caused by bacteria and fungi.

Mixtures of a solid vehicle or carrier and a liquid vehicle or carrier may be those of an inorganic solid vehicle or carrier, organic solid vehicle or carrier, and a liquid vehicle or carrier.

Of the above-described compositions, those comprising a thiol-silver complex, an organic solid vehicle or carrier, and if needed, a liquid vehicle or carrier find applications in quite a wide variety of industrial fields. Particularly, they are suitably used as surface-coating compositions applicable to surfaces of furniture, floor materials, walls, automobiles, and citrus fruits so as to give polish, to protect or to maintain their properties. Thiol-silver complexes, due to their solubility, in water, of not less than 1% by weight at 20° C., are particularly preferred as they do not cause precipitation of crystals when prepared into surface-coating compositions.

In compositions for coating surfaces, waxes and water-dispersible resins may be incorporated as solid vehicles or carriers. Compositions containing a wax and a water-dispersible resin are particularly suitable for use on floors or the like as floor polishing compositions.

Water-dispersible resins are polymers dispersible and emulsifiable in water, and they are used as so-called O/W type emulsions. These polymers are roughly divided into rubber-like polymers and resin-like polymers. Examples of rubber-like polymers include, for example, natural rubbers, ethylene-propylene-diene rubbers (EPDM), styrene-butadiene rubbers (SBR), chloroprene rubbers (CR), and acrylonitrile-butadiene rubbers (NBR). Examples of resin-like polymers include, for example, natural resins such as pine resin, polyethylenes, styrene-butadiene resins, vinyl resins (such as polyvinyl acetate, ethylene-vinyl acetate copolymers, and polyvinyl chloride), polyvinyl butyrals, polystyrenes, acrylic resins, and urethane resins. Of these, acrylic resin emulsions and vinyl resin emulsions are advantageously used in preparing floor polishing compositions from the viewpoints of gloss and compatibility with waxes.

In surface-coating compositions, emulsifiers may be incorporated in order to facilitate the production of emulsions and/or dispersions and to enhance their stabilities. Emulsifiers may be cationic, anionic, or nonionic. Cationic emulsifiers include quaternary ammonium salts; anionic emulsifiers include higher alcohol sulfates and amine soaps; and nonionic emulsifiers include ethers of polyethylene glycol (such as diethylene glycol monoethylether), carboxymethylcellulose, proteins, vegetable rubbers, and arginates. Emulsifiers are selected in consideration of the types of ions, HLB (hydrophile lipophile balance) values, and chemical structures. Since thiol-silver complexes are used in alkaline pH ranges, cationic and nonionic emulsifiers are preferred.

The compositions of the present invention may also contain, in addition to emulsifiers, various additives. For example, plasticizers may be incorporated to adjust the hardness. Other substances may also be used including defoamers such as tributyl phosphate, octyl alcohols, and silicone oils, thickeners such as methylcellulose, ammonium polyacrylate, and polyvinyl alcohol, freezing stabilizers such as ethylene glycol, volatile solvents such as cellosolves and alcohols, surfactants, dyes, perfumes, and antistatic agents.

Surface-coating compositions of the present invention are obtained by blending the above-described components. That is, generally speaking, a surface-coating composition of the invention comprises solid parts and an aqueous medium therefor, wherein the solid parts are constituted by thiol-silver complex, a solid vehicle or carrier (including wax and a water-dispersible resin), and a variety of additives. The thiol-silver complex may be added in a small amount as it is dispersed effectively and uniformly. The amount of a thiol-silver complex is 0.01–10.0%, preferably 0.1–5.0%, by weight based on that of a solid vehicle or carrier. Amounts less than 0.01% by weight cannot manifest sufficient antibacterial ability of the complex, whereas amounts in excess of 10.0% by weight decrease coating properties required for the composition, and thus, both cases are not preferred. From the viewpoints of physical properties, etc., the solid parts contained in a surface-coating composition of the present invention preferably accounts for 5–40% by weight of the composition, with 4–35% by weight of a solid vehicle or carrier, and 0–10% by weight of a volatile solvent. It is preferred that, based on the amount of the total solid parts, 30–50% by weight account for water-dispersible resin components, 5–25% by weight for wax components, and 5–25% for plasticizers. In surface-coating compositions, amounts less than 5% by weight or greater than 40% by weight are not preferred for the solid parts because proper viscosities for coating cannot be obtained. Solid vehicles or carriers should not be used in amounts less than 4% or in excess of 35% in order to avoid reduction in properties of resultant coats. Also, it is noted that if the amount of a water-dispersible component in solid parts is less than 30% by weight, problems occur in resultant coats, and if in excess of 50% by weight, hard coats are obtained, which is not preferable. Wax components in amounts less than 5% by weight may reduce smoothness and gloss and those in amounts greater than 25% by weight are not preferred either because excessive smoothness is caused.

When compositions of the present invention are used in reservoirs or as water-processing agents for developers, deterioration of water due to bacteria or fungi can be prevented. In compositions of the invention to be used for these purposes as water-processing agents, it is preferred that thiol-silver complexes be directly anchored onto solid carrier particles, or thiol-silver complexes and aqueous binders be anchored onto solid carrier particles. Particularly, water-processing compositions in which solid carrier particles are coated with a thiol-silver complex and an aqueous binder are preferred.

Solid carrier particles used herein are not particularly limited so long as they are insoluble in water. They preferably have average diameters between 10 μm and 10 mm, and preferably between 500 μm and 5 mm. Examples of the particles include aforementioned inorganic solid carrier particles (metal, glass, ceramics, etc.) and organic solid carrier particles (plastics, etc.).

As aqueous binders, aforementioned water-dispersible resins or water-soluble resins may be used.

Water-processing compositions are obtained, for example, by coating solid carrier particles with a composition comprising a thiol-silver complex and an aqueous binder, using a method such as immersion coating, fluidized bed coating, or spray coating, with a thickness of about 0.1–20 μm, preferably, 1–5 μm.

When the thus-obtained water-processing compositions are introduced into reservoirs or vessels containing developers, damage due to bacteria and fungi can be prevented for prolonged periods.

EXAMPLES

The present invention will next be described by way of examples, which should not be construed as limiting the invention. In the following Examples, parts and % are intended to mean parts by weight and % by weight unless otherwise indicated.

Example 1

Thiosalicylic acid (6.17 g) was dissolved in ethanol (200 ml). Silver nitrate (6.79 g) dissolved in ion-exchange water (10 ml) was gradually added to the thiosalicylic acid in ethanol by way of stirring. After stirring for about 1 hour, the resulting complex was collected through centrifugal separation (3,500 rpm×5 min). The recovered complex was washed with water four times (under centrifugal conditions of 3,500 rpm×5 min), and then washed sequentially with ethanol and acetone three times each (under centrifugal conditions of 10,000 rpm×10 min). The complex after washing was air-dried to yield an orange-colored powdery complex (code No. #1L-8H). Yield was approximately 9.7 g.

Properties of the obtained complex are shown below.

(1) IR spectrum

Disappearance of absorption attributed to SH in the vicinity of 2550 $cm^{-1}$.

Carboxyl group remained as —COOH due to absorption by C=O in the vicinity of 1700 $cm^{-1}$ and broad absorption by OH in the range of 3300–2200 $cm^{-1}$. Also, in the vicinity of 3400 $cm^{-1}$, there was observed absorption presumably attributed to crystal water.

(2) Thermal analysis

Decomposition: approx. 317° C.

(3) Elementary analysis (% by weight, calculated values in parentheses)

C; 30.79 (32.65), H; 1.92 (1.94), S; 11.5 (12.4),

O; 11.9 (12.4), N; 0.2 or less (–), Na; 0.1 or less (–), Ag; 43.0 (41.9).

From the above data, the chemical formula is considered to be $(C_7H_5O_2SAg)_2 \cdot 0-1H_2O$.

(4) ESCA (Electron Spectroscopy for Chemical Analysis)

A peak of an S2p spectrum was shifted from 164 ev (S-H) to 162.8 ev (S-M).

(5) NMR

Chemical shifts of $^1H$- and $^{13}C$-NMR are shown in Table 1.

TABLE 1

|  |  | 1 | 2 | 3 | 4 | 5 | 6 | 7 |
|---|---|---|---|---|---|---|---|---|
| $^{13}C$ | Thiosalicylic acid | 132.5 | 128.2 | 139.6 | 131.3 | 132.3 | 124.6 | 169.9 |
|  | #1L-8H | 129.9 | 137.2 | 141.6 | 138.0 | 129.7 | 123.7 | 172.2 |
|  | Chemical shift | –2.6 | +9.0 | +2.0 | +6.7 | –2.6 | –0.9 | +2.3 |

|  |  | a | d | c | b | e |
|---|---|---|---|---|---|---|
| $^1H$ | Thiosalicylic acid | 8.38 |  | 7.52 | 7.30 | 7.15 | 11.30 |
|  | #1L-8H | 7.85 |  | 8.19 | 6.81 | 6.91 | 13.96 |
|  | Chemical shift | –0.53 |  | 0.67 | –0.49 | –0.24 | 2.66 |

The chemical structure predicted from the above data is as follows.

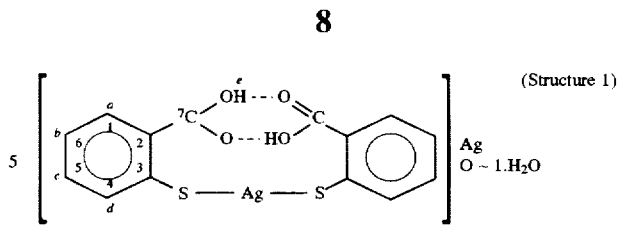

(Structure 1)

Example 2

Thiosalicylic acid (6.17 g) was dissolved in a 0.5N NaOH solution (200 ml). Silver nitrate (6.79 g) dissolved in ion-exchange water (10 ml) was gradually added to the thiosalicylic acid dissolved in alkali solution by way of stirring. After stirring for about 1 hour, insoluble matter was removed. To the supernatant (216 ml) obtained by centrifugal separation, an equivalent volume of ethanol was added while stirring to cause a complex to precipitate for collection (3,500 rpm×5 min). The recovered complex was dissolved in water and subjected to centrifugal separation (10,000 rpm×10 min) to collect a supernatant. To the supernatant (278 ml) was added an equivalent volume of ethanol by way of stirring to cause the complex to precipitate for collection (3,500 rpm×5 min). The recovered complex was again dissolved in water and centrifugally separated (10,000 rpm× 10 min) to obtain a supernatant. To the supernatant (310 ml) was added an equivalent volume of ethanol while stirring to cause the complex to precipitate for collection (3,500 rpm×5 min). The recovered complex was washed sequentially with ethanol and acetone three times each (under centrifugal conditions of 3,500 rpm×5 min). The complex after washing was air-dried to yield a yellow powdery complex (code No. #1L-8J). Yield was approximately 10 g.

Properties of the obtained complex are shown below.

(1) IR spectrum

Disappearance of absorption attributed to SH in the vicinity of 2550 $cm^{-1}$.

Carboxylic absorption in the vicinity of 1700 $cm^{-1}$ was shifted down to 1550 and 1400 $cm^{-1}$, indicating the group COOH has changed to $COO^-$.

Disappearance of OH absorption attributed to COOH in the vicinity of 3300–2200 $cm^{-1}$.

Also, in the vicinity of 3400 $cm^{-1}$, there was observed OH absorption presumably attributed to crystal water.

(2) Thermal analysis

Decomposition: approx. 302° C.

Loss of weight was observed in the vicinity of 100° C. which was presumably attributed to dewatering of crystal water.

(3) Elementary analysis (% by weight, calculated values in parentheses)

C; 27.32 (27.91), H; 2.15 (1.99), S; 10.2 (10.7),

O; 16.4 (15.9), N; 0.2 or less (–), Na; 6.92 (7.64),

Ag; 36.4 (35.9).

From the above data, the chemical formula is considered to be $(C_7H_4O_2SAgNa)_2 \cdot 2-3H_2O$.

(4) ESCA (Electron Spectroscopy for Chemical Analysis)

Sifting similar to that observed in the complex in Example 1 was obtained.

(5) NMR

Chemical shifts of $^1H$- and $^{13}C$-NMR are shown in Table 2.

TABLE 2

|  |  | 1 | 2 | 3 | 4 | 5 | 6 | 7 |
|---|---|---|---|---|---|---|---|---|
| $^{13}C$ | Sodium thiosalicylate | 132.0 | 138.8 | 138.2 | 128.3 | 133.4 | 128.7 | 177.6 |
|  | #1L-8J | 129.4 | 145.2 | 134.9 | 138.6 | 131.0 | 127.7 | 180.6 |
|  | Chemical shift | −2.6 | +6.4 | −3.3 | +10.3 | −2.4 | −1.0 | +3.0 |

|  |  | a |  |  | d | c | b |
|---|---|---|---|---|---|---|---|
| $^{1}H$ | Sodium thiosalicylate | 7.74 |  |  | 7.71 | 7.29 | 7.39 |
|  | #1L-8J | 7.18 |  |  | 7.35 | 6.62 | 7.03 |
|  | Chemical shift | −0.56 |  |  | −0.36 | −0.67 | −0.36 |

The chemical structures predicted from the above data are as follows.

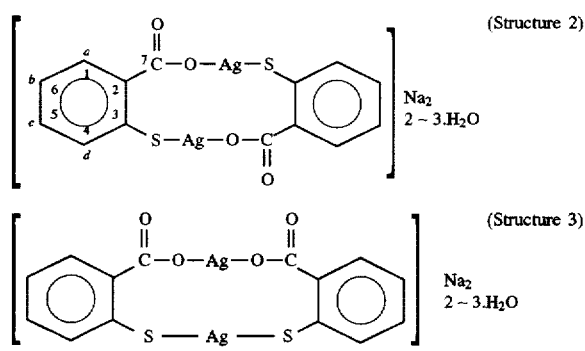

(Structure 2)

(Structure 3)

Example 3

Thiosalicylic acid (6.17 g) was dissolved in ethanol (140 ml). Silver nitrate (6.79 g) dissolved in ion-exchange water (20 ml) was gradually added to the ethanol solution of thiosalicylic acid by way of stirring. After stirring for about 1 hour, the resulting complex was collected through centrifugal separation (3,500 rpm×5 min). The pH of the recovered complex was adjusted to 12.5 by the addition of an aqueous barium hydroxide solution. The complex was collected through centrifugal separation (3,500 rpm×5 min). The recovered complex was washed with water six times (under centrifugal conditions of 6,000 rpm×10 min), and then washed sequentially with ethanol and acetone twice each (under centrifugal conditions of 6,000 rpm×10 min). The complex after washing was air-dried to yield a yellow powdery complex (code No. #1L-8P). Yield was approximately 15 g.

Example 4

Thiomalic acid (4.51 g) was dissolved in water (60 ml). Silver nitrate (3.40 g) dissolved in water (40 ml) was gradually added to the aqueous thiomalic solution by way of stirring. Ethanol (200 ml) was added to the resulting solution. Subsequently, 2N NaOH was added until yellow precipitates were formed. The precipitates were recovered (under centrifugal conditions of 3,500 rpm×5 min), followed by washing with ethanol and acetone three times each (under centrifugal conditions of 3,500 rpm×5 min). The complex after washing was air-dried to yield a yellow powdery complex (code No. #4). Yield was approximately 4.2 g.

Properties of the obtained complex are shown below.

(1) IR spectrum

Disappearance of absorption attributed to SH in the vicinity of 2550 $cm^{-1}$.

Absorptions were observed at 1700, 1550, and 1400 $cm^{-1}$.

At 3400 $cm^{-1}$, OH (monomer) from crystal water or from carboxyl group was observed.

(2) Thermal analysis

Decomposition: in the vicinity of 188° C.

(3) Elementary analysis (% by weight, calculated values in parentheses)

C; 16.67 (17.06), H; 1.74 (1.78), S; 11.1 (10.8),

O; 25.0 (24.4), N; 0.1 or less (−), Na; 8.0 (7.33),

Ag; 37.5 (38.3).

From the above data, the chemical formula is considered to be $(C_4H_4O_4SAgNa)_2.0-2H_2O$.

(4) NMR

Chemical shifts of $^{1}H$- and $^{13}C$-NMR are shown in Tables 3 and 4.

TABLE 3

|  |  | a(q*¹) | b(m*²) |
|---|---|---|---|
| $^{1}H$ | Thiomalic acid | 3.81 | 2.96 |
|  | #4 | 4.06 | 2.97 |
|  | Chemical shift | +0.25 | +0.01 |

*¹: split into 4
*²: split into 8

TABLE 4

|  |  | 1 | 2 | 3 | 4 |
|---|---|---|---|---|---|
| $^{13}C$ | Thiomalic acid | 38.8 | 42.0 | 177.1 | 178.9 |
|  | #4 | 44.8 | 47.9 | 179.4 | 183.0 |
|  | Chemical shift | +6.0 | +5.9 | +2.3 | +4.1 |

The chemical structures predicted from the above data are as follows.

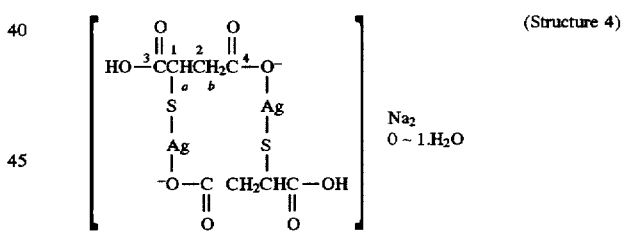

(Structure 4)

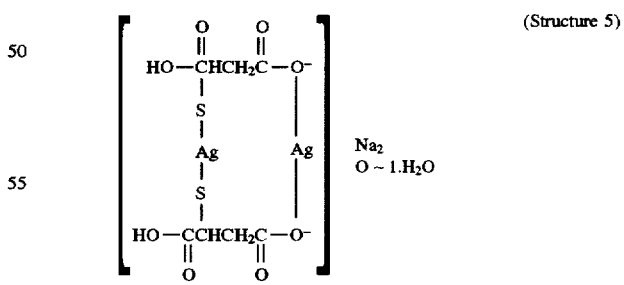

(Structure 5)

Example 5

(Synthesis of compounds)

Different thiol-containing ligands were reacted with silver ions under a variety of synthesizing conditions to produce complexes as shown in Tables 5 and 6.

TABLE 5

| Ligands | Code No. | Ligand (mmole) | NaOH (mmole) | AgNO₃ (mmole) | pH | Yield (g) | Color |
|---|---|---|---|---|---|---|---|
| p-Toluene thiol | #2 | 10.0 | — | 10.0 | | | Yellow |
| 2-Naphthalene thiol | #3 | 10.0 | — | 10.0 | | | Cream yellow |
| Thioglycolic acid | #5-a | 10.0 | — | 5.0 | | 0.90 | Orange |
| | #5-b | 10.0 | — | 10.0 | | 1.90 | Orange |
| | #5-c | 10.0 | — | 19.3 | | 3.12 | Light yellow |
| Thioglycolic acid.Na | #6-a | 10.0 | — | 5.0 | | 0.97 | White |
| | #6-b | 10.0 | — | 10.0 | | 1.92 | White |
| | #6-c | 10.0 | — | 19.3 | | 3.15 | White |
| β-Thiolactic acid | #7-a | 10.0 | — | 5.0 | 2.15 | 1.01 | White |
| | #7-b | 10.0 | — | 10.0 | 2.15 | 2.03 | White |
| | #7-c | 10.0 | — | 20.0 | 2.15 | 3.71 | White |
| | #8-a | 10.0 | 11.3 | 5.0 | 7.05 | 0.91 | Light yellow |
| | #8-b | 10.0 | 11.3 | 10.0 | 7.05 | 2.02 | Light yellow |
| | #8-c | 10.0 | 11.3 | 20.0 | 7.05 | 3.64 | White |
| α-Thiolactic acid | #9-a | 10.0 | — | 5.0 | 1.7 | 1.05 | Light yellow |
| | #9-b | 10.0 | — | 10.0 | 1.7 | 1.90 | Light yellow |
| | #9-c | 10.0 | — | 20.0 | 1.7 | 3.23 | Light yellow |
| | #10-a | 10.0 | 10.8 | 5.0 | 7.28 | 1.12 | Light yellow |
| | #10-b | 10.0 | 10.8 | 10.0 | 7.28 | 1.10 | Light yellow |
| | #10-c | 10.0 | 10.8 | 20.0 | 7.28 | 3.37 | Light yellow |
| L-Cysteine | #11-a | 10.0 | — | 5.0 | 5.03 | 1.30 | Yellow |
| | #11-b | 10.0 | — | 10.0 | 5.03 | 2.70 | White |
| | #11-c | 10.0 | — | 20.0 | 5.03 | 4.86 | Milky |
| | #12-a | 10.0 | 10.0 | 5.0 | 9.31 | 3.39 | White |
| | #12-b | 10.0 | 10.0 | 10.0 | 9.31 | 2.40 | Milky |
| | #12-c | 10.0 | 10.0 | 20.0 | 9.31 | 4.04 | Light yellow |
| | #13-a | 10.0 | 20.3 | 5.0 | 11.97 | 1.77 | Yellow |
| | #13-b | 10.0 | 20.3 | 10.0 | 11.97 | 2.70 | Yellow |
| | #13-c | 10.0 | 20.3 | 20.0 | 11.97 | 3.80 | Gray |
| α-Thioglycerol | #14-a | 10.0 | — | 5.1 | 4.09 | 1.00 | Light orange |
| | #14-b | 10.0 | — | 10.1 | 4.09 | 2.04 | Light orange |
| | #14-c | 10.0 | — | 20.2 | 4.09 | 0.76 | Light orange |
| | #15-a | 10.0 | 10.2 | 5.1 | 12 | 0.03 | Orange |
| | #15-b | 10.0 | 10.2 | 10.1 | 12 | 2.08 | Gray |
| | #15-c | 10.0 | 10.2 | 20.2 | 12 | 3.56 | Green black |

TABLE 6

| Ligands | Code No. | Ligand (mmole) | NaOH (mmole) | AgNO₃ (mmole) | pH | Yield (g) | Color |
|---|---|---|---|---|---|---|---|
| 5-Mercapto-(1H)-tetrazoyl acetic acid.Na | #16-a | 10.0 | — | 5.0 | 2.88 | 1.48 | White |
| | #16-b | 10.0 | — | 10.1 | 2.88 | 2.66 | White |
| | #16-c | 10.0 | — | 20.1 | 2.88 | 3.63 | White |
| | #17-a | 10.0 | 10.5 | 5.0 | 12.02 | 1.51 | White |
| | #17-b | 10.0 | 10.5 | 10.1 | 12.02 | 3.00 | Light gray |
| | #17-c | 10.0 | 10.5 | 20.1 | 12.02 | 3.70 | Dark gray |
| 2-Mercaptoethanol | #18-a | 10.0 | — | 5.0 | | 0.88 | Light yellow |
| | #18-b | 10.0 | — | 10.0 | | 1.73 | Light yellow |
| | #18-c | 10.0 | — | 20.0 | | 2.86 | White |
| Thiophenol | #21 | 10.0 | — | 10.0 | | | |
| 2,3-Dimercapto-succinic acid | #22-b | 1.0 | — | 1.0 | | 0.27 | Yellow |
| | #23-b | 1.0 | 2.0 | 1.0 | | 0.20 | Yellow |
| | #24-b | 1.0 | 4.0 | 1.0 | | 0.24 | Gray |
| 2-Mercaptobenzimidazole | #25 | 10.0 | — | 10.0 | | 2.13 | Cream |
| 2-Mercaptobenzothiazole | #26 | 10.0 | — | 10.0 | | 2.31 | Yellow |
| Thiourea | #27 | 10.0 | — | 10.0 | | 1.60 | Gray |
| Mercaptonicotinic acid | #36-1 | 10.0 | 20.0 | 10.0 | 8.00 | 2.84 | Yellow |
| | #36-2 | 10.0 | 20.0 | 5.0 | 12.00 | 1.40 | Yellow |
| | #36-3 | 10.0 | 20.0 | 15.0 | 7.00 | 1.58 | Cream yellow |
| | #36-4 | 10.0 | — | 10.0 | 2.00 | 2.49 | Yellow |
| 2-Thiouracil | #37-1 | 10.0 | 15.0 | 5.0 | 12.00 | 1.23 | Yellow |
| | #37-2 | 10.0 | 15.0 | 10.0 | 11.00 | 2.17 | White |
| | #37-3 | 10.0 | — | 5.0 | 7.00 | 1.18 | Yellow |
| 2-Thiohypoxanthine | #38-1 | 10.0 | 15.0 | 15.0 | 11.00 | 1.27 | White |
| | #38-2 | 10.0 | 15.0 | 20.0 | 7.00 | 3.86 | Yellow |

IR spectra of all the synthesized complexes were measured. As a result, it was confirmed that absorption attributed to S-H found in the vicinity of 2550 cm$^{-1}$ in starting materials of most compounds disappeared in complexes. Presumably, this is because the S-H bond had changed into other bonds such as S-Ag-. It was also confirmed that complexes having a carboxyl group had taken the form of COOH (1700 cm$^{-1}$) or COO$^-$ (1550 and 1400 cm$^{-1}$) depending on synthetic conditions.

Test Example 1. (Measurement of antibacterial activities)

Using the measuring methods (a) and (b) below, antibacterial activities of the complexes shown in Tables 7 and 8 were measured.

(a) Method for measuring antibacterial activity using a surface-smearing method

A potato dextrose (PD) agar medium (15 ml) was placed in a 90 mm petri dish and solidified. A spore suspension was prepared by suspending 3-5 platinum loop-amounts of spores, which had been cultured in advance in slant culture, in 5 ml of an aqueous solution containing 0.017% of a surfactant (Labisol B-30), and then by filtered using gauze.

A thiol-silver complex (about 10 mg) and a spore suspension (0.1 ml) were mixed and spread on the agar surface using a conraji stick, followed by culturing for 4 days at 25° C. After culturing, proliferation of spores was compared with that of a control which contained no test complexes, and antibacterial activities were assessed. Ranking of antibacterial activities are represented by "+", which indicates up to 80% of proliferation with respect to the proliferation level of the control (=100%, -), "++", which indicates up to 40% of proliferation, and "+++", which indicates almost complete suppression of proliferation.

(b) Method for measuring antibacterial activity based on a minimal inhibitory concentration (MIC)

Bacteria

A bacterium was inoculated in a soybean casein digest (SCD) liquid medium (5 ml) and precultured for 24 hours at 35° C. The precultured bacterial liquid was diluted so as to obtain a 100-fold diluted liquid (0.1 ml), and was inoculated into an SCD liquid medium containing a thiol-silver complex (2 ml). After performing shaking culture for 48 hours at 35° C., presence or absence of proliferation was assessed.

Yeast

Yeast was inoculated in a glucose-peptone (GP) liquid medium (5 ml) and precultured for 24 hours at 35° C. The precultured bacterial liquid was diluted so as to obtain a 100-fold diluted liquid (0.1 ml), and was inoculated into a GP liquid medium containing a thiol-silver complex (2 ml). After performing shaking culture for 48 hours at 35° C., presence or absence of proliferation was assessed.

Antibacterial activities measured for the tested complexes are shown in Tables 7 and 8.

TABLE 7

| | Surface-smearing method | | | | Minimal Inhibitory Concentration (μg/ml) | | | | | |
|---|---|---|---|---|---|---|---|---|---|---|
| Code No. | Aspergillus flavus | Penicillium chrysogenum | Cladosporium cladosporoides | Fusarium oxysporum | E. coli | S. aureus | B. subtilis | P. aerugi-nosa | S. cerevi-siae | C. albi-cans |
| #1L-8H | − | ++ | +++ | ++ | <2 | 16 | <2 | 16 | 125 | 1000 |
| #1L-8J | − | − | ++ | − | <2 | 32 | <2 | 16 | 125 | 1000 |
| #1L-8P | | | | | | 125 | | 16 | | |
| #2 | − | − | ++ | − | 62.5 | 1000 | 62.5 | 1000 | 125 | 1000 |
| #3 | + | + | +++ | − | 8 | 250 | <2 | 250 | 62.5 | 125 |
| #4 | − | + | ++ | + | 31.3 | >2000 | >2000 | 31.3 | 3.9 | >2000 |
| #6-c | − | + | ++ | + | | | | | | |
| #7-c | + | ++ | +++ | ++ | | | | | | |
| #8-c | ++ | +++ | +++ | ++ | | | | | | |
| #9-a | − | − | ++ | − | | | | | | |
| #9-c | ++ | ++ | +++ | ++ | | | | | | |
| #10-c | + | ++ | +++ | ++ | | | | | | |
| #11-a | − | + | ++ | + | | | | | | |
| #11-c | ++ | +++ | +++ | +++ | | | | | | |
| #12-b | − | − | ++ | − | | | | | | |
| #12-c | + | ++ | ++ | ++ | | | | | | |
| #13-c | +++ | +++ | +++ | +++ | | | | | | |

TABLE 8

| | Surface-smearing method | | | | Minimal Inhibitory Concentration (μg/ml) | | | | | |
|---|---|---|---|---|---|---|---|---|---|---|
| Code No. | Aspergillus flavus | Penicillium chrysogenum | Cladosporium cladosporoides | Fusarium oxysporum | E. coli | S. aureus | B. subtilis | P. aerugi-nosa | S. cerevi-siae | C. albi-cans |
| #14-a | − | + | +++ | − | | | | | | |
| #14-b | − | + | ++ | − | 62.5 | 250 | 250 | 62.5 | 250 | >1000 |
| #14-c | + | ++ | +++ | ++ | | | | | | |
| #15-b | − | + | ++ | + | | | | | | |
| #15-c | +++ | +++ | +++ | +++ | | | | | | |
| #16-b | + | +++ | +++ | ++ | 16 | 32 | 32 | 16 | 125 | 250 |

TABLE 8-continued

| | Surface-smearing method | | | | | | Minimal Inhibitory Concentration (μg/ml) | | | | |
|---|---|---|---|---|---|---|---|---|---|---|---|
| Code No. | Aspergillus flavus | Penicillium chrysogenum | Cladosporium cladosporoides | Fusarium oxysporum | E. coli | S. aureus | B. subtilis | P. aerugi- nosa | S. cerevi- siae | C. albi- cans |
| #16-c | + | +++ | +++ | +++ | | | | | | |
| #17-b | ++ | +++ | +++ | + | | | | | | |
| #17-c | +++ | +++ | +++ | +++ | | | | | | |
| #18-b | − | + | ++ | − | 250 | 1000 | 1000 | 250 | 500 | 1000 |
| #18-c | +++ | +++ | +++ | +++ | | | | | | |
| #36-1 | − | + | +++ | + | | | | | | |
| #36-2 | − | + | +++ | + | | | | | | |
| #36-3 | − | + | +++ | ++ | | | | | | |
| #36-4 | − | +++ | +++ | ++ | | | | | | |
| #37-2 | +++ | +++ | +++ | ++ | | | | | | |
| #37-3 | − | + | − | ++ | | | | | | |
| #38-1 | − | + | − | ++ | | | | | | |
| #38-2 | +++ | +++ | +++ | +++ | | | | | | |

As is apparent from Tables 7 and 8, the thiol-silver complexes of the present invention exhibited excellent antibacterial and antifungal activities on the bacteria and fungi.

Test Example 2. (Stability against exposure to light)

To 10 mg of each of the thiol-silver complexes shown in Table 9 to be tested, 1 ml of ethanol was added and then sonicated so as to disperse particles. The dispersed particles were uniformly fixed onto a Kiriyama filter paper (No. 3, diameter: 21 mm) by the application of a suction force. After drying, test pieces of the filter paper were sandwiched between colorless transparent plastic films (each having a thickness of 0.1 mm) and the peripheries were sealed.

The test pieces were exposed to sunlight outdoors on a sunny day. During the test, they were placed such that their surfaces received direct rays of the sun at an incidence angle of approximately 90°.

Measurement was performed using a color difference meter CR-300 (using $D_{65}$ rays) manufactured by Minolta Camera Co., Ltd. Six hours after exposure to sunlight, measurement was reiterated 4 times and the data were averaged. The results were represented in an L*a*b* color representation system according to CIF 1976. The results are shown in Table 9.

TABLE 9

| | Before exposure to sunlight | | | After exposure to sunlight | | |
|---|---|---|---|---|---|---|
| Filter alone | 92.3 | 0.1 | 1.8 | 92.4 | 0.2 | 1.7 |
| #1L-8H | 83.1 | 13.2 | 66.4 | 65.4 | 8.3 | 40.1 |
| #1L-8J | 94.6 | −11.7 | 34.4 | 90.8 | −9.3 | 34.8 |
| #4 | 93.4 | −10.4 | 27.2 | 64.2 | 16.6 | 31.0 |
| #36-2 | 91.8 | −7.5 | 19.1 | 87.0 | −3.0 | 34.1 |
| #37-2 | 92.4 | −5.5 | 4.4 | 61.8 | 13.3 | 18.8 |
| #38-2 | 87.4 | −0.7 | 33.0 | 84.1 | −0.6 | 7.8 |

As is apparent from Table 9, the thiol-silver complexes of the present invention have excellent stability against exposure to light.

Test Example 3. (Safety test)

Peroral toxicity (single dose, ICR, male) of the complexes shown in table 10 was investigated. The results obtained on day 14 of administration are shown in Table 10.

TABLE 10

| Tested complexes | Dose (mg/kg) | Dead mice/Total mice |
|---|---|---|
| #1L-8J | 5000 | 5/5 |
| | 2500 | 1/5 |
| | 1250 | 0/5 |
| | 625 | 0/5 |
| #1L-8H | 3871 | 0/4 |
| | 2978 | 0/4 |
| | 2291 | 0/5 |
| | 1762 | 0/5 |

As is apparent from Table 10, it was demonstrated that the thiol-silver complexes of the present invention are very safe.

In this connection, the $LD_{50}$ of #1L-8J was 2.5–5.0 g/kg, whereas that of #1L-8H was not less than 3.9 g/kg.

Test Example 4 (measurement of anti-human cytomegalovirus (HCMV) activities)

Using starting materials obtained by suspending or dissolving a complex #4, #1L-8H, or #1L-8J in an MEM containing 2% fetal bovine serum; hereinafter referred to as 2% MEM) so as to achieve a concentration of 1 mg/ml, measurement was performed under the below-described conditions.

Reaction liquid

The titers of HCMV were adjusted to 1× $10^3$ pfu/ml in Experiment 1 and to 1×$10^4$ pfu/ml in Experiment 2. To 1 ml of 2% MEM were added HCMV and 50, 10 or 1 μg of each compound.

Cells

Human fetal lung cells (HEL) (10th–14th in passage) were inoculated in the number of 1×$10^4$ cells in a Lab-Tekchamber.

Method

The above reaction liquid was occasionally stirred at room temperature and incubated for 1 hour. HEL was infected with 0.5 ml of the resultant liquid, and the infected cells were cultured at 37° C. in a $CO_2$ incubator.

Experiment 1: Culturing was performed for 72 hours without changing the medium.

Experiment 2:
(1) Culturing was performed for 72 hours without changing the medium, and
(2) After 1 hour of adsorption, washing was performed twice using 2% MEM, followed by culturing for 72 hours under $CO_2$ by adding 0.5 ml of the same medium.

Assessment

Antiviral activities were assessed using a fluorescent antibody staining method. Briefly, a Microtrak kit (manufactured by Syva) containing an anti-preinitial stage protein antibody and an anti-initial stage protein antibody) was used for fluorescent staining. The lower the number of cells stained with fluorescence, the stronger the antiviral activity. In a single field of vision under a fluorescent microscope, approximately 400 cells were observed.

Using the above-described conditions, the number of cells which were positive in fluorescent staining was counted upon completion of Experiment 1 in a single field of vision of a fluorescent microscope. The results are shown in Table 11.

TABLE 11

| Complex | Concentration of compounds (μg/ml) | | | |
|---|---|---|---|---|
| | 0 | 50 | 10 | 1 |
| Control | 30 | — | — | — |
| #4 | — | 20 | 30 | 20 |
| #1L-8H | — | — | 5 | — |
| #1L-8J | — | — | 10 | 10 |

Separately, after completion of each of (1) and (2) of Experiment 2, the number of cells which were positive in fluorescent staining was counted in a single field of vision of a fluorescent microscope. The results are shown in Tables 12 and 13.

TABLE 12

| Complex | Concentration of compounds (μg/ml) | | | |
|---|---|---|---|---|
| | 0 | 50 | 10 | 1 |
| Control | 390 | — | — | — |
| #4 | — | 220 | 300 | — |
| #1L-8H | — | 100 | 240 | 280 |
| #1L-8J | — | 150 | 130 | 170 |

TABLE 13

| Complex | Concentration of compounds (μg/ml) | | | |
|---|---|---|---|---|
| | 0 | 50 | 10 | 1 |
| Control | 120 | — | — | — |
| #4 | — | 70 | 80 | 80 |
| #1L-8H | — | 20 | 30 | 30 |
| #1L-8J | — | 20 | 20 | 30 |

As is apparent from Tables 11 through 13, the thiol-silver complexes of the present invention exhibited remarkable antiviral activities.

Examples 6 and 7 and Comparative Example 1
(An example using a thermoplastic resin)

Into 60 parts of a polyethylene wax (product of Sanyo Chemical Industries, Ltd., "Sanwax 131-P", softening point: 108° C.), 40 parts of a thiol-silver complex shown in Table 14 which had been dried in advance through heating were added and melt-dispersed using triple rollers heated to 110°–120° C. so as to prepare a master batch. The thus-obtained master batch (2.5 parts) was diluted through kneading together with a low density polyethylene (product of Asahi Chemical Industry Co., Ltd., "Santech F-1920", softening point: 220° C.) (97.5 parts) on dual rollers heated to 210°–230° C. The kneaded and diluted master batch was pressurized at 210°–230° C. for 0.5 min. under a pressure of 150 kg/m² so as to prepare test specimens each having a thickness of 1 mm.

Examples 8, 9 and Comparative Example 2
(An example using a thermoplastic resin)

Into 99 parts of polypropylene (product of Ube Industries, Ltd., "J-109G", softening point: 260° C.), 1 part of a thiol-silver complex shown in Table 14 which had been dried in advance through heating was added and melt-dispersed using a pressurizing kneader at a vicinity of 250° C. The resulting material was pressurized at 260°–280° C. for 0.5 min. under pressure of 150 kg/m² to prepare test specimens each having a thickness of 1 mm.

Examples 10, 11 and Comparative Example 3
(An example using a thermosetting resin)

Into 50 parts of an epoxy resin (product of Ciba-Geigy, "Araldite GY-260"), 50 parts of a thiol-silver complex shown in Table 14 which had been dried in advance through heating were added, followed by kneading and dispersing using triple rollers to prepare a paste containing a high concentration of a thiol-silver complex. Two parts of this paste having a high concentration and 88.1 parts of the epoxy resin were kneaded and diluted using triple rollers, after which 9.9 parts of a hardener (product of Ciba-Geigy, "HY-951") were blended. The resultant material was poured into a mold and cured so as to obtain test specimens each having a thickness of 1 mm.

Examples 12, 13 and Comparative Example 4
(An example using a thermosetting resin)

Into 100 parts of an acrylic polyol (product of Dainippon Ink and Chemicals, Inc., "Acrydic A-850", solid matter: 70%), 1 part of a thiol-silver complex shown in Table 14 which had been dried in advance through heating was added, followed by kneading using a marler. Forty (40) parts of polyisocyanate (product of Dainippon Ink and Chemicals, Inc., "Barnock DN-950", solid matter: 75%) were blended therewith. The resultant blend was poured into a mold and cured so as to obtain test specimens each having a thickness of 1 mm.

(Antibacterial Test)

Onto each of the surfaces of test specimens measuring 5×5 cm² obtained in Examples 6 through 13 and in Comparative Examples 1 through 4 was sprayed a bacterial liquid shown in Table 14, and the test specimens were subjected to culturing for 24 hours. After culturing, the degree of bacterial proliferation was compared with that of a control containing no thiol-silver complexes, thereby evaluating antibacterial activities. Ranking of antibacterial activities are represented by "–", which indicates the bacterial proliferation degree in the same level as the control, "+", which indicates up to 50% of proliferation with respect to the proliferation level of the control, and "++", which indicates almost complete suppression of proliferation. The results are shown in Table 14.

TABLE 14

| Thiol-silver complex | Aspergillus flavus | Penicillium chrysogenum | Cladosporium cladosporoides | Fusarium oxysporum | E. coli | S. aureus | B. subtilis | P. aureginosa | C. albicans |
|---|---|---|---|---|---|---|---|---|---|
| Example 6 (#1L-8H) Thiosalicylic acid-silver complex | − | + | ++ | ++ | ++ | ++ | ++ | ++ | + |
| Example 7 (#3) 2-Naphthalenethiol-silver complex | + | + | ++ | − | ++ | + | ++ | − | + |
| Example 8 (#1L-8H) Thiosalicylic acid-silver complex | − | + | ++ | + | + | + | + | + | + |
| Example 9 (#14-b) α-Thioglycerol-silver complex | − | − | + | + | − | − | + | + | − |
| Example 10 (#1L-8H) Thiosalicylic acid-silver complex | − | + | ++ | + | ++ | ++ | + | + | + |
| Example 11 (#14-b) α-Thioglycerol-silver complex | − | + | ++ | + | + | + | + | + | − |
| Example 12 (#1L-8H) Thiosalicylic acid-silver complex | − | + | ++ | ++ | + | + | ++ | ++ | + |
| Example 13 (#16-b) 5-Mercapto-(1H)tetrazoylacetic acid-silver complex.Na | − | + | + | − | + | + | + | ++ | + |
| Comparative Example 1 Sanaizol 100*[1] | + | + | ++ | ++ | + | − | − | − | − |
| Comparative Example 2 Amorden KM-75*[2] | + | − | − | − | − | − | − | − | − |
| Comparative Example 3 Amorden KM-75*[2] | − | − | − | − | + | + | − | − | − |
| Comparative Example 4 Sanaizol 100*[1] | + | + | ++ | + | − | − | − | − | − |

*[1]Product of San-ai Oil Co., Ltd.: Thiabendazole
*[2]Product of Daiwa Chemical Industry Co., Ltd.

Example 14
[Preparation of surface-coating compositions]

An 5% aqueous solution of #1L-8J was prepared, and formulated as shown in Table 15. The components were mixed and stirred so as to obtain a composition for coating surfaces (floor polishing composition).

TABLE 15

| Emulsion of a synthetic resin (Effective solid components: 40%) | 40 parts by weight |
|---|---|
| Aqueous carnauba wax dispersion (Effective solid components: 40%) | 5 parts by weight |
| Dispersion of dibutylphthalate (Effective solid components: 40%) | 5 parts by weight |
| Ethylcellosolve | 10 parts by weight |
| Aqueous #1L-8J solution (5%) | 2 parts by weight |
| Water | 38 parts by weight |

[Assessment of physical properties]

The resultant composition was assessed against a composition vinyl floor tile (semihard CT; product of Tajima Co., Ltd.) in terms of various physical properties including anti-heelmark properties, antislipping properties, waterproofness, resistance against detergents, ease in removal (immersion method), and gloss (after three application times) in accordance with JIS K3920. The results are shown in Table 16.

TABLE 16

| Anti-heelmark properties | Good |
|---|---|
| Antislipping properties | 0.55 |
| Waterproofness | Good |
| Resistance against detergents | Good |
| Ease in removal (Immersion method) | Good |
| Gloss (after three application times) | 51% |

The compositions of the present invention exhibited satisfactory results in terms of any of the above properties required for floor polishing compositions, proving that they are advantageously used as floor polishing compositions.

[Assessment of antibacterial activities]

Four different compositions similar to those described in Table 15, excepting that the amount of #1L-8J was varied to 0% (W-1), 0.1% (W-2), 0.5% (W-3), and 1.0% (W-4), were prepared and tested for antibacterial activities against E. coli and Bacillus subtilis.

Each of the compositions was permeated into gauze, thinly applied onto an OHP sheet which had been cut so as to have a size measuring 10 cm×10 cm, and then dried for 30 minutes at room temperature. Three cycles of this operation were conducted. The resultant OHP sheets were cut into disks having a diameter of 2.1 cm for use as specimen sheets (4 specimens). Four 12-well plates were provided for subjecting the 4 specimens to duplicate tests, and each sheet was placed in a well of each of the 12-well plates. That is, a single 12-well plate was used for a single species of bacterium. Specimen sheets to which no compositions were applied were used as controls, and each was placed in the remaining wells (2 wells) of each well plate.

One platinum loop-amount of each species of the bacteria was inoculated in a soybean casein digest (SCD) liquid medium (5 ml) and subjected to shaking culture at 35° C. for 24 hours. Thereafter, the resultant culture was diluted to 2×10³-fold in the case of E. coli cultures, and to 1×10³-fold in the case of B. subtilis cultures.

To each well, 0.2 ml of the corresponding thus diluted bacterial liquid was inoculated, followed by standing culture at 35° C. for 24 hours.

After culturing, each well was washed with 1.8 ml of PBS to recover the bacteria. The bacteria were subjected to sequential 10-fold dilutions using sterilized water. 0.1 ml of each of the diluted liquids was inoculated onto 2 sheets of SCD agar medium. In order to elevate the detection limit of the neat liquid, 1 ml of the neat liquid was inoculated onto a single SCD agar medium (detection limit; <2) and cultured at 35° C. for 24 hours. When colonies were not detected, a further 24 hour-culture was performed under the same conditions.

The number of inoculated bacteria was determined as follows: 0.2 ml of each of the above-mentioned diluted liquids was added to each well; the well was washed with 1.8 ml of PBS to recover bacteria, and the washings were then subjected to sequential 10-fold dilutions using sterilized water to prepare 10-fold–$10^4$-fold diluted liquids. 0.1 ml of each diluent was inoculated onto 2 sheets of SCD agar medium, followed by culturing at 35° C. for 24 hours; and the number of bacteria contained in the culture was counted. The results are shown in Table 17.

TABLE 17

| Specimen | No. of inoculated bacteria | No. of bacteria after 24 hours |
|---|---|---|
| Strain: E. coli | | |
| W-1 (0% contained) | 3.0 × 10$_5$ | 2.6 × 10$^4$ |
|  |  | 1.6 × 10$^4$ |
| W-2 (0.1% contained) |  | <2 |
|  |  | <2 |
| W-3 (0.5% contained) |  | <2 |
|  |  | <2 |
| W-4 (1.0% contained) |  | <2 |
|  |  | <2 |
| No application |  | 9.2 × 10$^5$ |
|  |  | 9.0 × 10$^5$ |
| Well alone |  | 5.6 × 10$^5$ |
|  |  | 1.1 × 10$^6$ |
| Strain: B. subtilis | | |
| W-1 (0% contained) | 2.1 × 10$_4$ | 1.7 × 10$^4$ |
|  |  | 2.5 × 10$^4$ |
| W-2 (0.1% contained) |  | 20 |
|  |  | 40 |
| W-3 (0.5% contained) |  | 100 |
|  |  | 100 |
| W-4 (1.0% contained) |  | 20 |
|  |  | 20 |
| No application |  | 4.0 × 10$^4$ |
|  |  | 1.6 × 10$^4$ |
| Well alone |  | 5.4 × 10$^4$ |
|  |  | 1.1 × 10$^5$ |

As is apparent from Table 17, the compositions of the present invention (W-2, W-3, and W-4) exhibited excellent antibacterial and antifungal activities. In contrast, the composition containing no thiol-silver complexes (W-1) did not exhibit antibacterial or antifungal activities.

Comparative Example 5

It was attempted to prepare a surface-coating composition having a formulation similar to that described in Example 14, using instead of #1L-8J, a metal-containing compound, i.e., silver chloride powder (obtained by reducing a powder product of Wako Pure Chemicals Industries, Ltd. to have an average particle diameter of not more than 1 μm) having a solubility, in water, in the amount of less than 1% by weight (20° C.). However, the metal-containing compound was not sufficiently dissolved, and as a result, only a poor dispersion was obtained. Thus, it was not possible to obtain a surface-coating composition exhibiting effective antibacterial and antifungal activities.

Comparative Example 6

It was attempted to prepare a surface-coating composition having a formulation similar to that described in Example 14 using bactericidal silver-on-solid zeolite particles (=solid zeolite particles on which silver is carried) instead of #1L-8J. However, the silver-on-solid zeolite particles were not uniformly dispersed, causing elevation in viscosity. Therefore, the composition could not be used as a surface-coating composition. This is presumably because the presence of the solid particles destroyed the emulsion of the synthetic resin.

Example 15

| 1) Polyvinyl alcohol (product of Nitto Chemical Industry, Co., Ltd.; Kasezole AV-15) | 70% by weight |
|---|---|
| 2) Purified water | 27% by weight |
| 3) #1L-8H (Reduced in an agate mortar to have an average particle diameter of 0.3 μm) | 3% by weight |

The above components were charged in a universal ball mill (manufactured by Yamato Science Co., Ltd.; 141 porcelain pot, 3 mmØ alumina porcelain balls, 40 rpm), and impact was applied for 20 hours to disperse #1L-8H so as to obtain a spray neat liquid. The following components:

| 4) the above-described spray neat liquid | 45% by weight |
|---|---|
| 5) propellant | 55% by weight | were put into a spray can and sealed to prepare an antibacterial and antifungal spray composition of the present invention.

Example 16

| 1) Acrylic emulsion (product of Toyo Ink Mfg. Co., Ltd.; Tocryl S-20) | 70% by weight |
|---|---|
| 2) Purified water | 22% by weight |
| 3) #1L-8J | 3% by weight |
| 4) Purified ethyl alcohol (product of Wako Pure Chemical Industries, Ltd.) | 5% by weight |

The above components were thoroughly mixed by stirring so as to dissolve a thiosalicylic acid-silver complex, thereby obtaining a spray neat liquid. Using this neat liquid, the procedure of Example 15 was repeated to obtain an antibacterial and antifungal spray composition of the present invention.

Example 17

| 1) Purified water | 92% by weight |
|---|---|
| 2) #1L-8J | 1% by weight |
| 3) Purified ethyl alcohol (product of Wako Pure Chemical Industries, Ltd.) | 5% by weight |
| 4) Wetting agent (product of Sannopco; Nopcowet SN-20T) | 0.5% by weight |

The above components were thoroughly mixed by stirring so as to dissolve a thiosalicylic acid-silver complex, thereby obtaining a spray neat liquid. Using this neat liquid, the procedure of Example 15 was repeated to obtain an antibacterial and antifungal spray composition of the present invention.

Comparative Example 7

| 1) Polyvinyl alcohol (product of Nitto Chemical Industry, Co., Ltd.; | 70% by weight |
|---|---|

-continued

| | |
|---|---|
| Kasezole AV-15) | |
| 2) Purified water | 27% by weight |
| 3) Zirconium phosphate-silver powder (product of Toagosei Chemical Industry Co., Ltd.; Novaron) | 3% by weight |

The above components were charged in a universal ball mill (manufactured by Yamato Science Co., Ltd.; 141 porcelain pot, 3 mmØ alumina porcelain balls, 40 rpm), and impact was applied for 20 hours to disperse zirconium phosphate-silver powder so as to obtain a spray neat liquid. The following components:

| | |
|---|---|
| 4) the above-described spray neat liquid | 45% by weight |
| 5) propellant | 55% by weight | were put into a spray can and sealed to prepare an antibacterial and antifungal spray composition.

Comparative Example 8

| | |
|---|---|
| 1) Purified water | 95% by weight |
| 2) Purified ethyl alcohol (product of Wako Pure Chemical Industries, Ltd.) | 5% by weight |
| 3) Wetting agent (product of Sannopco; Nopcowet SN-20T) | 0.5% by weight |

The above components were thoroughly mixed by stirring to obtain a spray neat liquid. Using this neat liquid, the procedure of Example 15 was repeated to obtain an antibacterial and antifungal spray composition.

Antibacterial and antifungal activities of each of the above-described antibacterial and antifungal spray compositions were assessed. In this connection, aqueous resins which may be used in the present invention are not particularly limited so long as they are able to affix the thiol-silver complex of the present invention onto surfaces of clothes, interior decorations, etc. which require antibacterial and antifungal effects, and thus, they are not limited only to those described in the above Examples. Aqueous resins and their proportions may be arbitrarily selected.

[Assessment of antibacterial and antifungal properties]
Assessment 1

Test pieces were prepared by applying a spray composition in amounts of 400±40 mg/tile onto floor P tiles (20 cm×20 cm) made of vinyl chloride, followed by drying, and subsequently applying a bacterial liquid containing one of the bacteria shown in Table 18.

Immediately after the application of the corresponding bacterial liquid, bacteria were collected from a 5 cm×5 cm area of each of the surfaces of these test pieces. The bacteria were cultured for 24 hours, and the amount of live bacteria after culturing was taken as the amount of bacteria used for coating.

Another set of the same type of test pieces was left for 24 hours in a laboratory room, and bacteria were similarly extracted from a 5 cm×5 cm area of each of the pieces. The extract was cultured for 24 hours, and the amount of live bacteria after culturing was taken as the amount of remaining bacteria.
Assessment 2

In a manner similar to that described in Assessment 1, test pieces were prepared by applying a spray composition onto cotton cloth (20 cm×20 cm) in amounts of 400±40 mg/cloth, followed by drying, and subsequently applying a bacterial liquid containing one of the bacteria shown in Table 19.

Immediately after the application of the corresponding bacterial liquid, a 5 cm×5 cm area of each of the test pieces were cut out and immersed in 50 ml of physiological saline solution, then bacteria were extracted. The extract was cultured for 24 hours, and the amount of live bacteria after culturing was taken as the amount of bacteria used for coating.

Another set of the same type of test pieces was left for 24 hours in a laboratory room, and bacteria were similarly extracted from a 5 cm×5 cm area of each of the pieces. The extract was cultured for 24 hours, and the amount of live bacteria after culturing was taken as the amount of remaining bacteria.
Standards for assessment Proportions of the remaining live bacteria with respect to the amounts of the bacteria used for coating were assessed based on the following standards:
"−"

The ratio of the amount of the remaining live bacteria to the amount of the bacteria used for coating is not less than 50%.
"+"

The ratio of the amount of the remaining live bacteria to the amount of the bacteria used for coating is less than 50% and not less than 10%.
"++"

The ratio of the amount of the remaining live bacteria to the amount of the bacteria used for coating is less than 10%.

The results of assessment are shown in Tables 18 and 19. It is understood that the antibacterial and antifungal spray compositions of the present invention exhibit antibacterial and antifungal activities significantly superior to those of the composition of Comparative Example 8 in which a thiol-silver complex was not used, or to those of the composition of Comparative Example 7 in which zirconium phosphate-silver was used.

TABLE 18

| | Ex. 15 | Ex. 16 | Ex. 17 | Comp. Ex. 7 | Comp. Ex. 8 |
|---|---|---|---|---|---|
| E. coli | ++ | ++ | ++ | + | − |
| Pseudomonas aeruginosa | + | ++ | ++ | − | − |
| Salmonella | + | ++ | ++ | − | − |
| Staphylococcus aureus | ++ | ++ | ++ | − | − |
| Bacillus subtilis | ++ | ++ | ++ | + | − |
| Candida yeast | + | ++ | ++ | − | − |
| Saccharomyces yeast | + | ++ | ++ | − | − |
| Black-koji mould | + | + | + | − | − |

TABLE 19

| | Ex. 15 | Ex. 16 | Ex. 17 | Comp. Ex. 7 | Comp. Ex. 8 |
|---|---|---|---|---|---|
| E. coli | ++ | ++ | ++ | − | − |
| Pseudomonas aeruginosa | + | ++ | + | − | − |
| Salmonella | + | ++ | ++ | − | − |
| Staphylococcus aureus | ++ | ++ | ++ | − | − |
| Bacillus | + | + | ++ | − | − |

TABLE 19-continued

|  | Ex. 15 | Ex. 16 | Ex. 17 | Comp. Ex. 7 | Comp. Ex. 8 |
|---|---|---|---|---|---|
| subtilis |  |  |  |  |  |
| Candida yeast | + | + | + | − | − |
| Saccharomyces yeast | + | + | + | − | − |
| Black-koji mould | + | + | + | − | − |

Example 18

A 3% aqueous solution of polyvinyl alcohol R-1130 manufactured by Kuraray Co., Ltd. was prepared. To the solution, #1L-8H and aluminum sulfate were added so that the concentrations of the former and latter compounds became 0.09% and 3%, respectively. The resultant mixture was sufficiently stirred, and 250 g of the mixture were applied, using a New Marumerizer manufactured by Fuji Powdal, to 750 g of glass beads having an average diameter of 1.4 mm. Subsequently, the beads were immersed in an aqueous aluminum sulfate solution for a whole day and night. The beads were heated at 120° C. for 10 minutes following removal of moisture. Excessive aluminum sulfate was washed off using purified water, and moisture was removed. The beads were heated at 120° C. for 10 minutes, followed by drying in vacuo at 70° C. to obtain specimen particles each having a coating of the composition.

Example 19

A 3% aqueous solution of polyvinyl alcohol R-1130 manufactured by Kuraray Co., Ltd. was prepared. To the solution, #1L-8J and aluminum sulfate were added so that the concentrations of the former and latter compounds became 0.09% and 3%, respectively. The resultant mixture was sufficiently stirred, and 250 g of the mixture were applied, using a New Marumerizer manufactured by Fuji Powdal, to 750 g of glass beads having an average diameter of 1.4 mm. Subsequently, the beads were immersed in an aqueous aluminum sulfate solution for a whole day and night. Following removal of moisture, the beads were heated at 120° C. for 10 minutes. Excessive aluminum sulfate was washed off using purified water, and moisture was removed. The beads were heated at 120° C. for 10 minutes, followed by drying in vacuo at 70° C. to obtain specimen particles each having a coating of the composition.

Comparative Example 9

A 3% aqueous solution of polyvinyl alcohol R-1130 manufactured by Kuraray Co., Ltd. was prepared. To the solution, aluminum sulfate was added so as to achieve a concentration of 3%. The resultant mixture was sufficiently stirred, and 250 g of the mixture were applied to 750 g of glass beads having an average diameter of 1.4 mm using a New Marumerizer manufactured by Fuji Powdal. Subsequently, the beads were immersed in an aqueous aluminum sulfate solution for a whole day and night. Following removal of moisture, the beads were heated at 120° C. for 10 minutes. Excessive aluminum sulfate was washed off using purified water, and moisture was removed. The beads were heated at 120° C. for 10 minutes, followed by drying in vacuo at 70° C. to obtain specimen particles each having a coating of the composition.

[Assessment of antibacterial activities]

Particles prepared in Examples 18, 19, and in Comparative Example 9 (2 g each) were placed in wells of 12-well plates.

As regards the bacteria, 1 platinum loop-amount of one of the species of bacteria was inoculated in a soybean casein digest (SCD) liquid medium (5 ml) and subjected to shaking culture at 35° C. for 24 hours. Thereafter, the resultant culture was diluted to 10-fold in the case of P. aeruginosa and L. pneumophila cultures, and to $10^2$-fold in the case of E. coli cultures.

For each specimen, ten wells were provided for a total of 5 specimens including 3 specimens from composition-coated particles, 1 specimen from composition-uncoated particles, and a blank (well alone), in a doubled manner. That is, a total of 10 wells were provided for the test of a single species of bacterium. To each well containing a specimen, 1 ml of the corresponding diluted bacterial liquid was inoculated, and to the wells containing no specimens, 0.2 ml of the corresponding diluted bacterial liquid was inoculated. The wells were subjected to standing culture at 35° C. for 24 hours. After culturing, each well was washed with 4 ml of sterilized physiological saline to recover bacteria. The bacteria were subjected to sequential 10-fold dilutions using sterilized physiological saline. 0.1 ml of each of the diluted liquids was inoculated onto 3 sheets of SCD agar medium, followed by culturing at 35° C. for 24 hours. When colonies were not detected, a further 24 hour-culture was performed under the same conditions. The number of bacteria was counted and taken as the number of remaining live bacteria.

From each of the wells containing no specimens, bacteria were recovered using 1.8 ml of sterilized physiological saline. The bacteria were subjected to sequential 10-fold dilutions using sterilized physiological saline. 0.1 ml of each of the diluted liquids was inoculated onto 3 sheets of SCD agar medium, followed by culturing at 35° C. for 24 hours. The number of bacteria was counted and taken as the number of inoculated bacteria.

Standards for assessment

Proportions of the remaining live bacteria with respect to the amounts of the inoculated bacteria were assessed based on the following standards:

"−"

The ratio of the amount of the remaining live bacteria to the amount of the inoculated bacteria is not less than 50%.

"+"

The ratio of the amount of the remaining live bacteria to the amount of the inoculated bacteria is less than 50% and not less than 10%.

"++"

The ratio of the amount of the remaining live bacteria to the amount of the inoculated bacteria is less than 10%.

The results of assessment are shown in Table 20. It is understood that the particles for water processing treated with the antibacterial and antifungal compositions of the present invention exhibit excellent antibacterial and antifungal activities.

TABLE 20

|  | Ex. 18 | Ex. 19 | Comp. Ex. 9 |
|---|---|---|---|
| P. aeruginosa | ++ | ++ | − |
| E. coli | ++ | ++ | − |
| L. pneumophila | ++ | ++ | − |

Industrial Applicability

The antibacterial, antifungal, and antiviral agents of the present invention have wide antibacterial and antifungal spectra, exhibit antiviral properties, are well compatible with a variety of vehicles and carriers, and sustain their effects for prolonged periods. Moreover, their peroral toxicities are low, and they are mild to the skin and mucosa. Therefore, they are useful in a wide variety of applications including textiles, sanitary goods, foods, vegetables and fruits, clean films, packaging materials, paints, glass filters for sterile rooms, and water-processing, etc. They are also advantageously used as antibacterial and antifungal sprays applicable to buildings, clothes, insoles of shoes, shoes, floor mats, etc.

Moreover, the agents of the invention are useful for preparing surface-coating compositions to give polish, as well as to protect or to maintain surfaces of furniture, floor materials, walls, automobiles, and citrus fruits.

In addition, they are useful not only for preventing bacterial infection caused by wounds and bedsores, but also for therapy therefor. Although emergence of antibiotic-resistant bacteria resulting from the use of large amounts of antibiotics has recently become a serious social problem, the antibacterial agents of the present invention can contribute significantly to solving this problem.

We claim:

1. A complex comprising a silver ion and a thiol group-containing compound, wherein the thiol group-containing compound is selected from the group consisting of p-toluene thiol, 2-naphthalene thiol, thioglycerol, 5-mercapto-(1H)-tetrazolyl acetic acid, 2,3-dimercaptosuccinic acid, thiophenol, 2-mercaptobenzimidazole, 2-mercaptobenzothiazole, mercaptonicotinic acid, thiouracil,and 2-mercaptohypoxanthine.

2. The complex of claim 1, wherein the molar ratio of the thiol group-containing compound to the silver ion is 0.1 to 4.

3. The complex of claim 1 or 2, further comprising a counter cation selected from the group consisting of $K^+$, $Na^{++}$, $Ca^{++}$, and $Ba^{++}$.

4. An antibiotic composition comprising the complex of claim 1.

5. The antibiotic composition of claim 4, wherein the antibiotic composition is an antibacterial composition, an antifungal composition, or an antiviral composition.

6. The antibiotic composition of claim 4, further comprising a carrier.

7. The antibiotic composition of claim 6, wherein the carrier is solid or liquid.

8. An antibiotic spray composition comprising a liquid carrier and a complex comprising a silver ion and a thiol group-containing compound, wherein the thiol group-containing compound is selected from the group consisting of thiosalicylic acid, p-toluene thiol, 2-naphthalene thiol, thiomalic acid, α-thiolactic acid, cysteine, thioglycerol, 5-mercapto-(1H)-tetrazolyl acetic acid, 2-mercaptoethanol, 2,3-dimercaptosuccinic acid, thiophenol, 2-mercaptobenzimidazole, 2-mercaptobenzothiazole, mercaptonicotinic acid, thiouracil, and 2-mercaptohypoxanthine.

9. The antibiotic spray composition of claim 8, wherein the antibiotic spray composition is an antibacterial spray composition or an antifungal spray composition.

10. An antibiotic spray composition comprising an aqueous binder, wherein the aqueous binder includes a water-dispersible resin or a water-soluble resin; and a complex comprising a silver ion and a thiol group-containing compound, wherein the thiol group-containing compound is selected from the group consisting of thiosalicylic acid, p-toluene thiol, 2-naphthalene thiol, α-thiolactic acid, cysteine, thioglycerol, 5-mercapto-(1H)-tetrazolyl acetic acid, 2-mercaptoethanol, 2,3-dimercaptosuccinic acid, thiophenol, 2-mercaptobenzimidazole, 2-mercaptobenzothiazole, thiourea, mercaptonicotinic acid, thiouracil, and 2-mercaptohypoxanthine.

11. The antibiotic spray composition of claim 10, wherein the antibiotic spray composition is an antibacterial spray composition or an antifungal spray composition.

12. The antibiotic spray composition of claim 10, wherein the aqueous binder includes polyvinyl alcohol.

13. An antibiotic composition comprising (a) a complex containing a silver ion and a thiol group-containing compound, wherein the thiol group-containing compound is not thiomalic acid; and (b) a carrier selected from the group consisting of inorganic solid vehicles, waxes, and resins.

14. The antibiotic composition of claim 13, wherein the antibiotic composition is an antibacterial composition, an antifungal composition, or an antiviral composition.

15. An antibiotic composition comprising (a) a complex containing a silver ion and a thiol group-containing compound, wherein the thiol group-containing compound is not thiomalic acid; and (b) a resin, wherein the complex is dispersed in the resin.

16. The antibiotic composition of claim 15, wherein the antibiotic composition is an antibacterial composition, an antifungal composition, or an antiviral composition.

17. The antibiotic composition of claim 15, wherein the resin is a thermoplastic resin.

18. The antibiotic composition of claim 15, wherein the resin is a thermosetting or energy beam-sitting resin.

19. A master batch comprising (a) a complex containing a silver ion and a thiol group-containing compound, and (b) a resin, wherein the amount of complex is at least 5% by weight of the composition.

20. The master batch of claim 19, wherein the amount of the complex is from 10% to 80% by weight of the composition.

21. A surface-coating composition comprising (a) a complex containing a silver ion and a thiol group-containing compound, wherein the thiol group-containing compound is not thiomalic acid; and (b) a resin or a wax.

22. A surface-coating composition comprising (a) a complex containing a silver ion and a thiol group-containing compound, wherein the thiol group-containing compound is not thiomalic acid; (b) a wax and (c) a water-dispersible resin.

23. A floor-polishing composition comprising (a) a complex containing a silver ion and a thiol group-containing compound, wherein the thiol group-containing compound is not thiomalic acid; (b) a wax and (c) an emulsion of an acrylic resin or a vinyl resin.

24. A composition comprising a complex and a aqueous binder, wherein the complex includes a thiol group-containing compound and a silver ion, the thiol group-containing compound is not thiomalic acid, the aqueous binder includes a water-dispersible resin, and the water-dispersible resin is substantially insoluble in water.

25. A composition comprising a complex and an aqueous binder, wherein the complex includes a thiol group-containing compound and a silver ion, the thiol group-containing compound is not thiomalic acid, and the aqueous binder includes polyvinyl alcohol.

26. Solid particles for water processing comprising an inorganic oxide, wherein the particles are coated with a composition, the composition contains a complex and an aqueous binder, and the complex includes a thiol group-containing compound and a silver ion.

27. Solid particles for water processing, wherein the particles are free of activated charcoal, the particles are coated with a composition, the composition contains a complex and an aqueous binder, and the complex includes a thiol group-containing compound and a silver ion.

* * * * *